United States Patent [19]

Nash

[11] 4,171,572
[45] Oct. 23, 1979

[54] LIGHT CONTROL APPARATUS FOR A DENTAL HANDPIECE

[75] Inventor: John E. Nash, Downington, Pa.

[73] Assignee: Star Dental Manufacturing Co., Inc., Conshohocken, Pa.

[21] Appl. No.: 863,289

[22] Filed: Dec. 22, 1977

[51] Int. Cl.² .................... A61C 1/10; G08B 1/00; H01V 1/00
[52] U.S. Cl. ................... 32/27; 32/DIG. 7; 32/DIG. 3; 340/309.1; 362/4; 362/32; 137/225; 307/141; 251/22
[58] Field of Search .......... 32/27, DIG. 7, DIG. 3, 32/22; 362/32, 295, 802, 804, 6, 3, 4, 5; 128/6, 395; 340/309.1, 309.2, 309.5, 562; 328/77; 307/141, 114; 137/225; 251/50, 53, 22

[56] References Cited

U.S. PATENT DOCUMENTS

| | | | |
|---|---|---|---|
| 2,539,828 | 1/1951 | Goldis | 32/DIG. 7 |
| 3,590,232 | 6/1971 | Sadowski | 32/27 |
| 3,739,373 | 6/1973 | Liming et al. | 340/309.1 |
| 3,806,081 | 4/1974 | Otto | 251/22 |
| 3,965,465 | 6/1976 | Alexander | 362/802 |
| 4,053,756 | 10/1977 | Takahashi | 362/32 |
| 4,060,724 | 11/1977 | Heine et al. | 362/32 |
| 4,082,961 | 4/1978 | Genuit | 307/141 |

Primary Examiner—Louis G. Mancene
Assistant Examiner—Michael Foycik
Attorney, Agent, or Firm—Tom M. Moran; Joseph I. Hirsch

[57] ABSTRACT

An apparatus for controlling the actuation of a light for illuminating the work zone adjacent the operative end of a dental handpiece. The apparatus includes (a) switch for actuating a light source when a signal is transmitted to the actuating switch from the power transmitting line for the dental handpiece, (b) line for transmitting the signal to the actuating switch from the power transmitting means for the handpiece, and (c) delay shutoff switch associated with the actuating switch for maintaining the light source on for a predetermined period of time after transmission of power to the operative end of the handpiece is terminated and then causing the light source to be extinguished at the end of the predetermined period of time.

58 Claims, 11 Drawing Figures

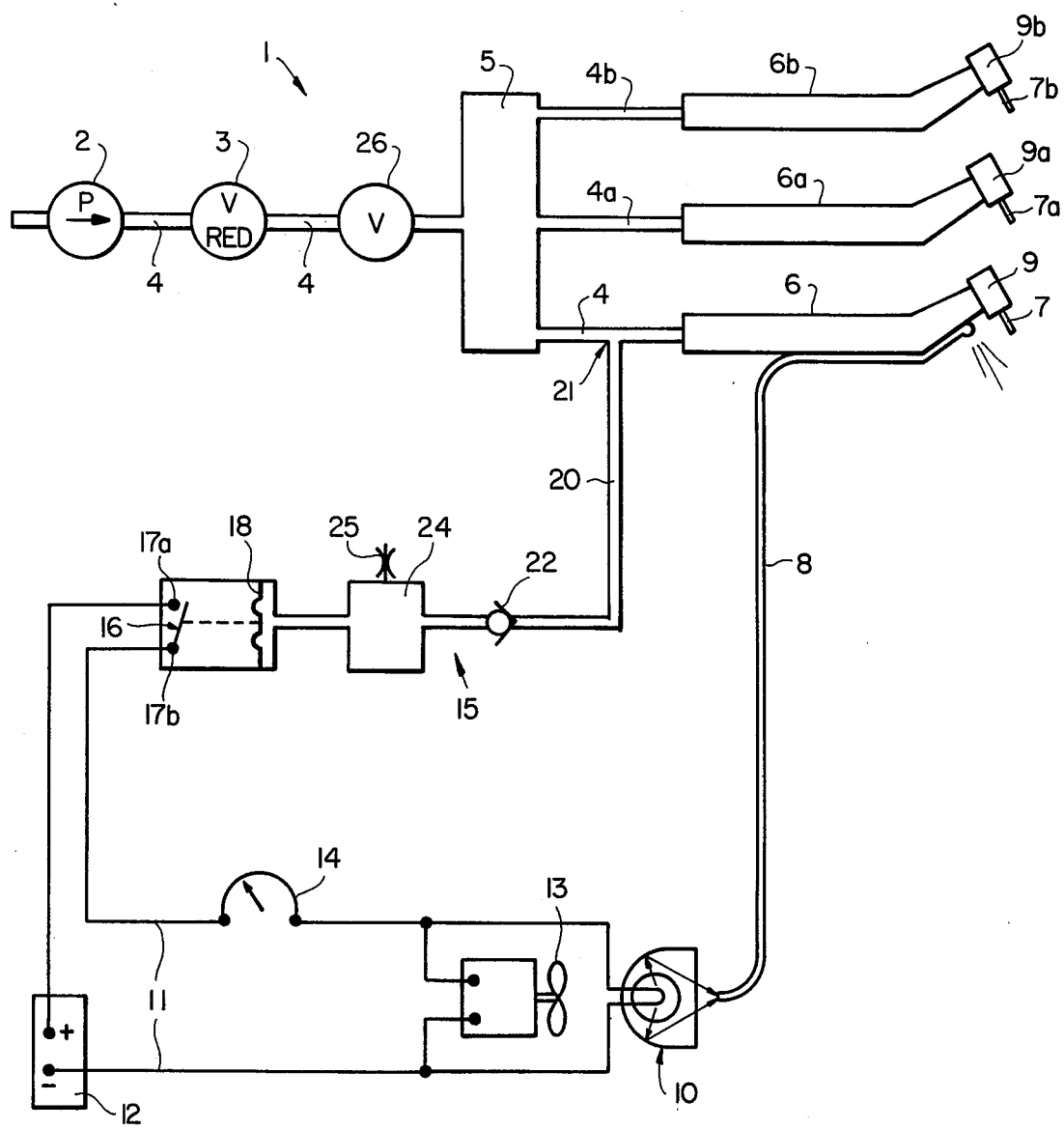
FIG_1
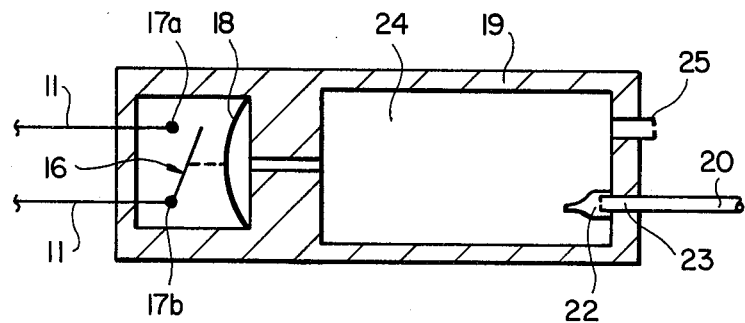
FIG_3

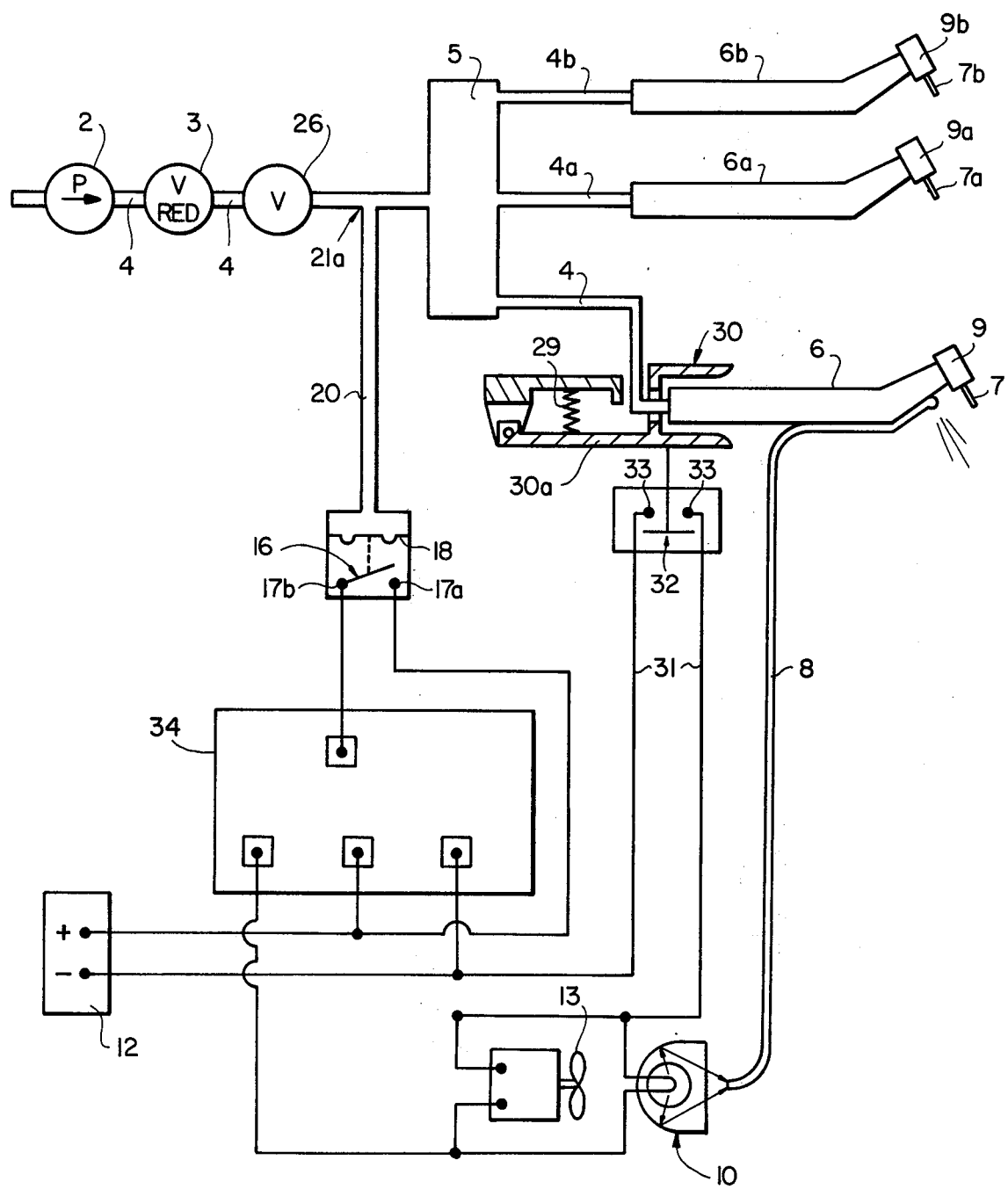
FIG_2

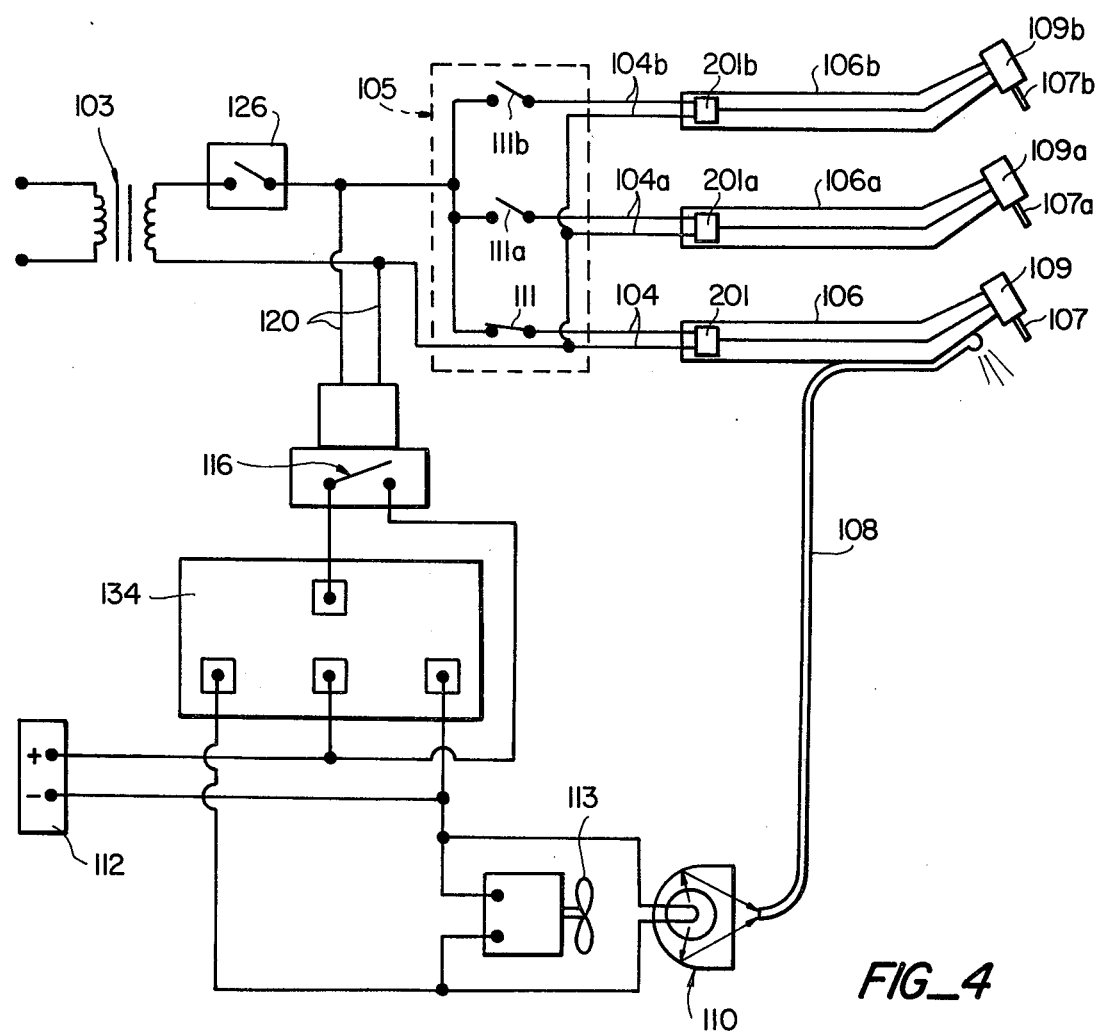
FIG_4
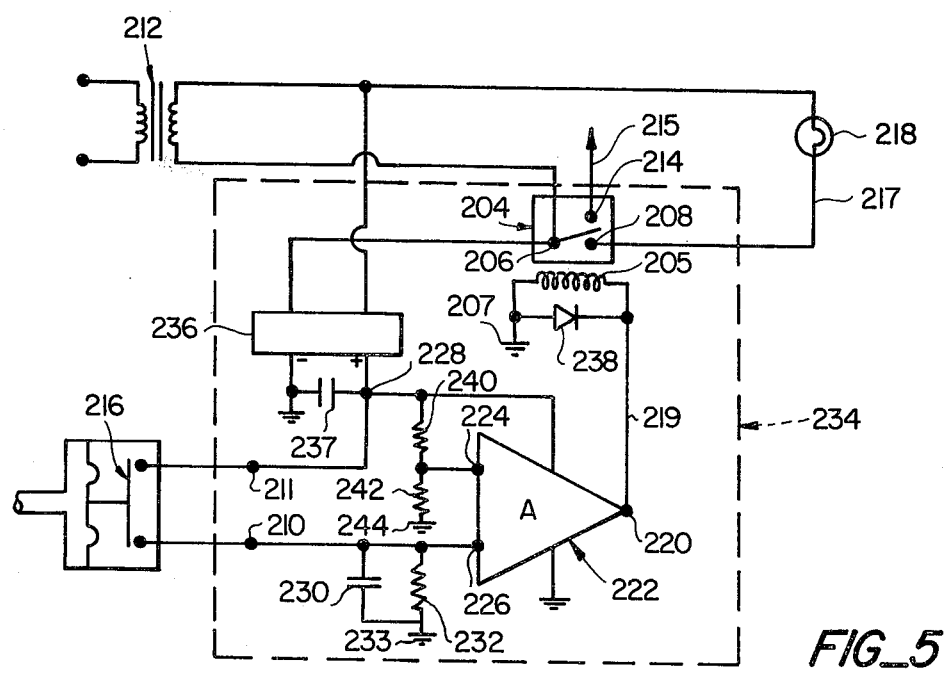
FIG_5

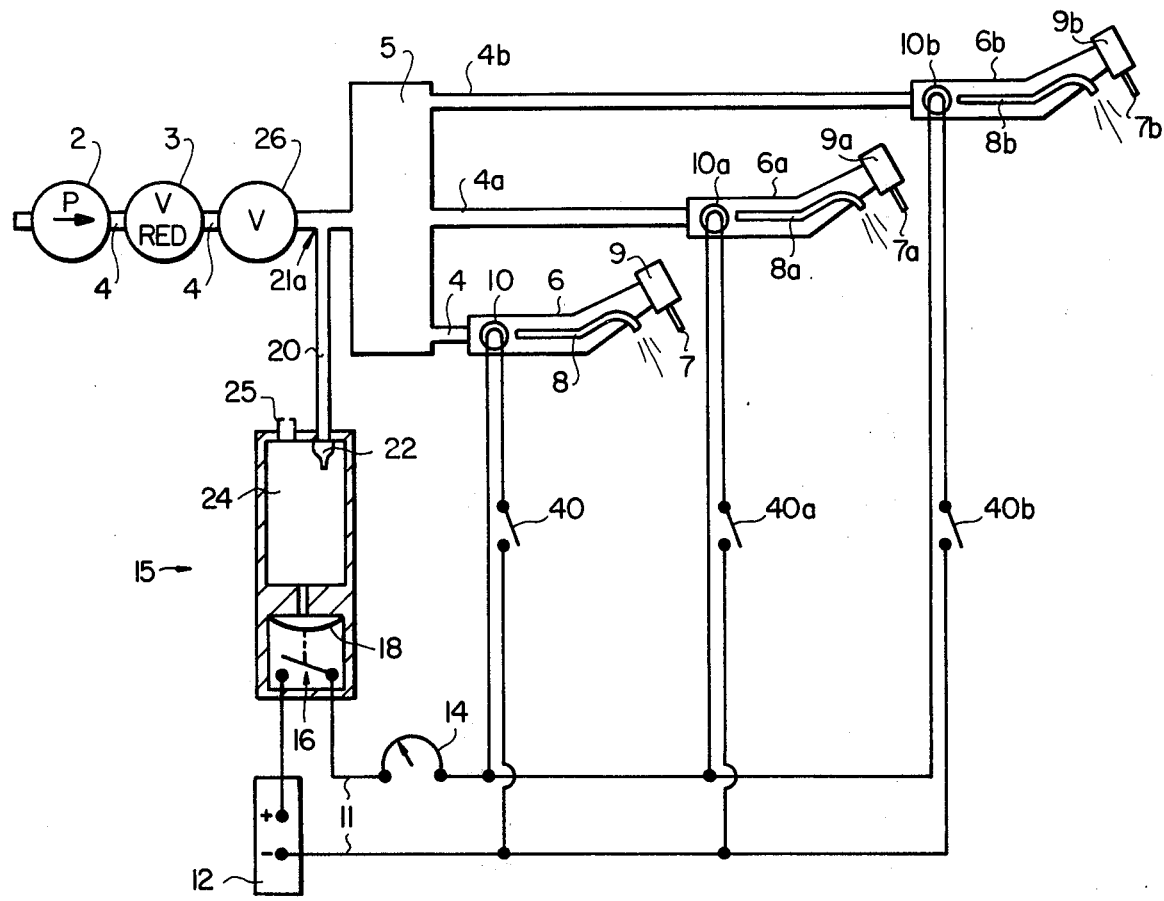
FIG_6
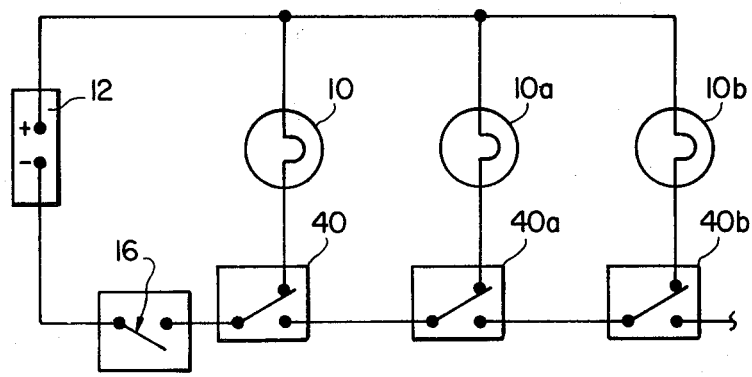
FIG_7

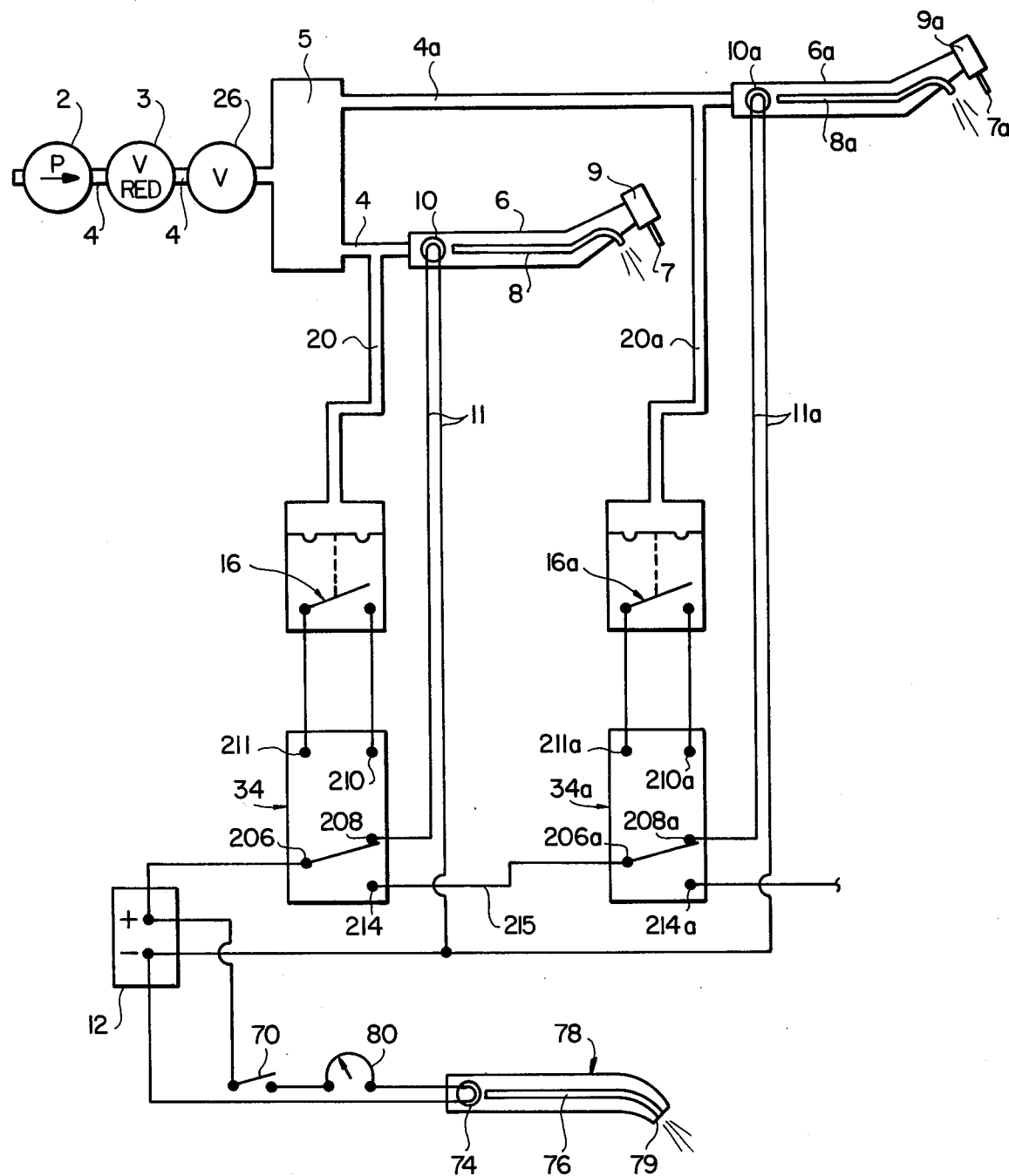
FIG_8

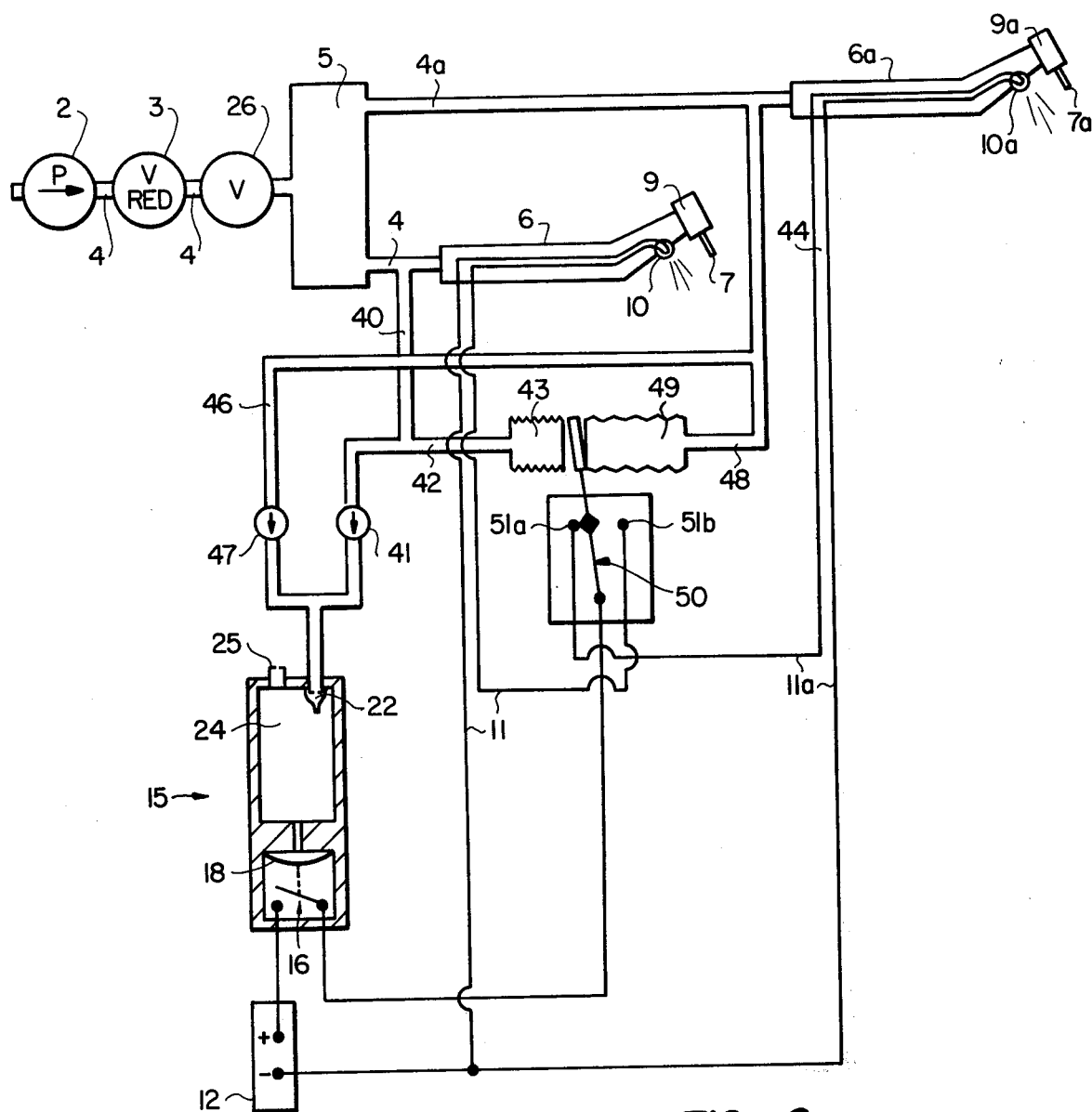
FIG_9
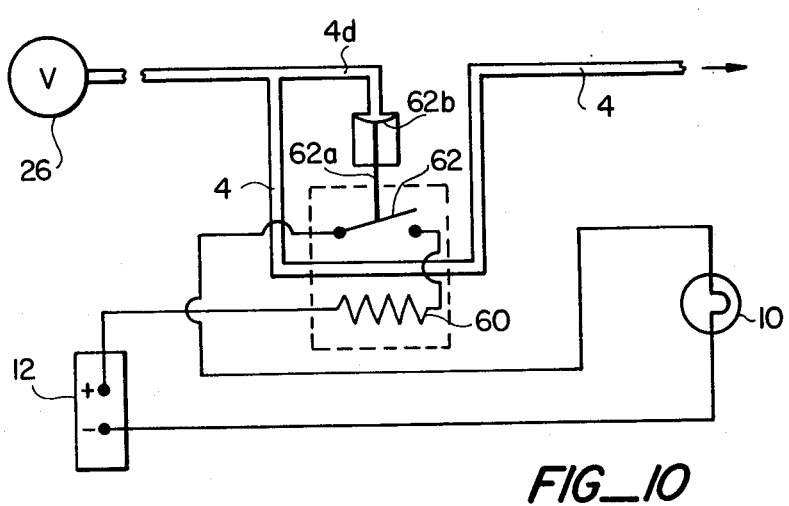
FIG_10

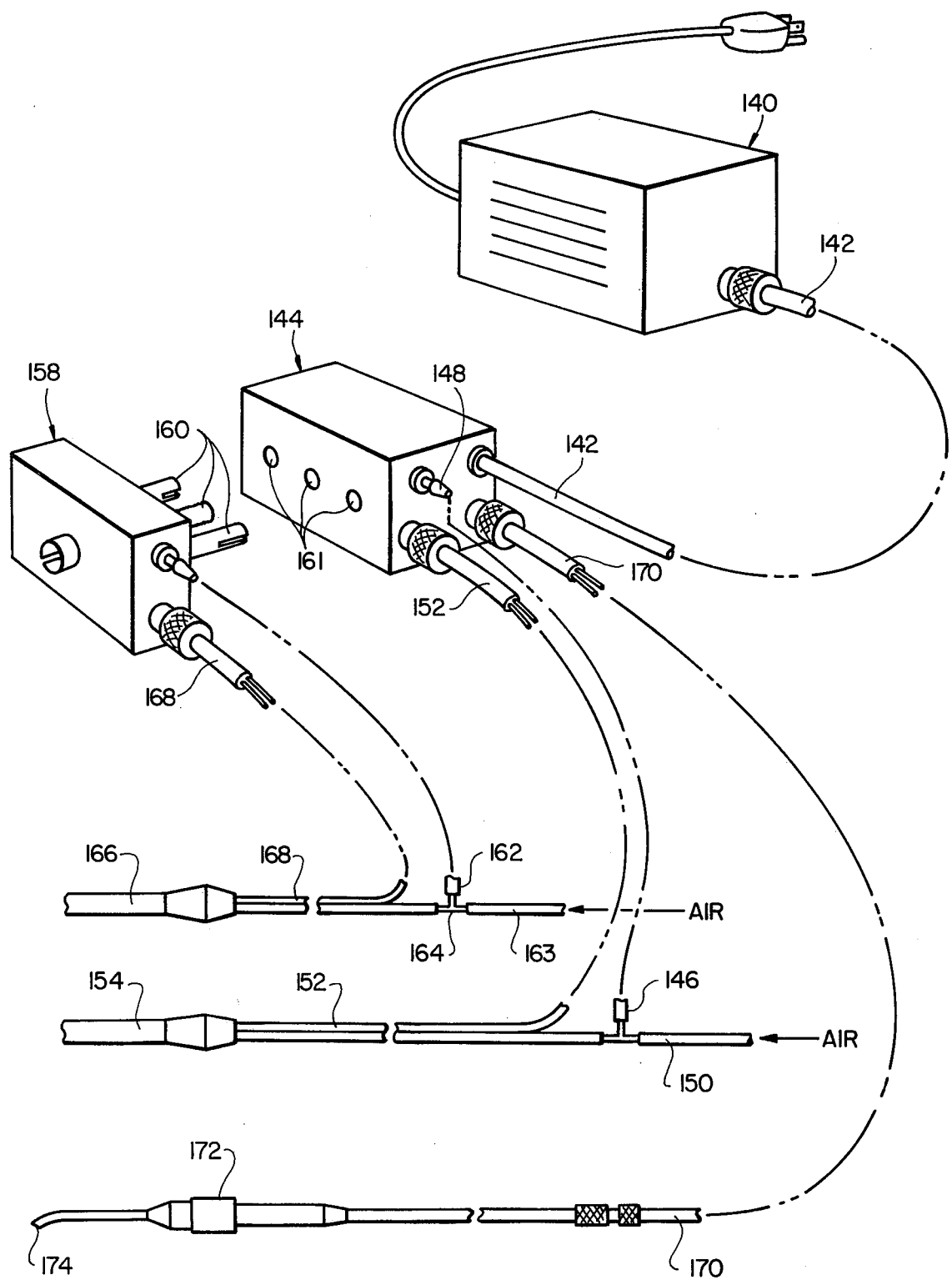
FIG_11

LIGHT CONTROL APPARATUS FOR A DENTAL HANDPIECE

BACKGROUND OF THE INVENTION

1. Field of the Invention

This invention relates to an improved apparatus for controlling the operation of an oral illumination system associated with a fluid driven or an electrically driven dental handpiece unit.

2. Prior Art

It is known that some dental handpiece units have associated therewith one or more fiber optic bundles which direct a beam of light to the region of a patient's tooth which is being drilled. See, for example, U.S. Pat. Nos. 2,539,828 to Goldis et al; 3,397,457 to Gosselin; 3,634,938 to Hutchinson; 3,638,013 to Keller; 3,683,503 to Klein; and 3,897,134 to Scrivo.

Other handpiece units have miniature lamps attached internally or externally at the turbine end of the handpiece to illuminate the area being drilled directly without the use of the fiber optic bundles. See U.S. Pat. No. 2,038,911 to Stutz et al; French Pat. No. 1,123,034 to Pestel; and German Pat. No. 853,494.

Prior art units provide light to the handpiece by:

(1) a manually operated on-off switch or (2) a hanger position switch that senses whether the handpiece is inoperative (in the hanger) or is being used (in the dentist's hand). In the first case, operation of the switch may interrupt the dentist's normal operating technique by causing momentary loss of concentration. In the second case if the dentist wishes to examine the burr or turbine after removing the handpiece from the hanger, he may have to look into the fiber optic light or miniature lamp which is already on. Because the issuing light is substantially brighter than ambient room illumination, the dentist may momentarily be "dazzled" and may need to pause briefly before resuming work on the patient.

The apparatus of this invention solves the problem of momentary dazzle by providing means to illuminate the oral cavity just prior to the dentist inserting the drill of the handpiece into the patient's mouth.

The apparatus of this invention also allows the light to remain lit for a predetermined period of time after drilling has ceased thereby enabling the dentist, if desired, to examine the drilled area with the aid of the light emitted at the operative end of the handpiece. The predetermined period of time can be varied as desired, and after the light is automatically extinguished the dentist may examine or change the burr, etc.

The apparatus of this invention also allows the dentist to illuminate a patient's mouth using the light associated with the handpiece prior to drilling by providing means to turn on the light and maintain it on for a predetermined period of time.

SUMMARY OF THE INVENTION

This invention is an apparatus for controlling the actuation of a light source for illuminating the work zone adjacent the operative end of a dental handpiece. The dental handpiece has an operative end; means to transmit power to the operative end; control means associated with the power transmitting means so that when the control means is actuated, power is transmitted to the operative end; and a light source for illuminating the region adjacent the operative end of the handpiece. The apparatus of the invention controls the actuation of the light-source and comprises (a) means for actuating the light-source when a signal is transmitted thereto; (b) means for transmitting a signal from the power transmitting means to the actuating means; and (c) delay shutoff means associated with the actuating means to maintain the light source on for a predetermined period of time after transmission of power to the operative end of the handpiece is terminated, and then causing the light source to be extinguished at the end of said predetermined period of time.

The control apparatus of this invention may be employed with an electrically or fluid driven dental handpiece, preferably the latter and especially the pneumatically driven type. The delay means may also be electrically or pneumatically operated. It is preferred that the control apparatus of this invention is employed with a light source and light transmitting means integral with the dental handpiece.

While the invention will be described in connection with specific embodiments described hereafter, it will be understood that it is not intended to limit the invention to the embodiments set forth. On the contrary, it is intended to cover all alternatives, modifications and equivalents as may be included within the spirit and scope of the invention as defined by the appended claims.

BRIEF DESCRIPTION OF THE DRAWINGS

FIG. 1 is a schematic diagram of a control apparatus for a pneumatically driven handpiece wherein a pneumatic switch regulates the actuation of a remote light for a fiber optic means and an air pressure accumulator provides a delay means to maintain the light on after the air supply is turned off.

FIG. 2 is a schematic diagram of a control apparatus for a pneumatically driven handpiece wherein a pneumtic switch regulates the actuation of a remote light for a fiber optic means and the delay means is an electrical circuit. An additional arming switch for the light is associated with the handpiece.

FIG. 3 is a cross-sectional view of a pneumatic delay means and switch particularly suitable for use in the invention shown in FIG. 1.

FIG. 4 is a schematic diagram of a control apparatus for an electrically driven dental handpiece wherein an electrically-actuated switch regulates the actuation of a remote light for a fiber optic means, and the delay means is an electrical circuit.

FIG. 5 is a circuit diagram of an electrical delay means for the light source.

FIG. 6 is a schematic diagram of a pneumtic control apparatus for a plurality of dental handpieces wherein a single switch and associated pneumatic delay means controls actuation of a plurality of lights, a separate light being integral with each of the handpieces being controlled.

FIG. 7 is a schematic diagram of a lighting system for FIG. 6 except that only one handpiece light is actuated at one time.

FIG. 8 is a schematic diagram of a pneumatic control apparatus for a plurality of dental handpieces wherein a pneumatic delay means and switch are associated with each handpiece, each handpiece having a light source adjacent the non-working end thereof and fiber optic means for transmitting the light emitted by the light source to the working end of the handpiece. In addition an independent fiber optic probe is shown.

FIG. 9 is a schematic diagram of a pneumatic control apparatus for two handpieces having a single pneumatic delay means and switch for a light in each of two handpieces, and means to energize the light in either handpiece, as desired.

FIG. 10 is a schematic diagram of a thermally actuated delay means and switch to control the actuation of a light-producing means.

FIG. 11 is a perspective view of the assembled apparatus schematically described in FIG. 8.

FURTHER DESCRIPTION OF THE INVENTION AND PREFERRED EMBODIMENTS

This invention relates to an apparatus for controlling the actuation of a light source to illuminate the region adjacent the operative end of a dental handpiece. The dental handpiece for purposes of this application can be any appropriate powered dental tool having at least one operative end. Examples of suitable dental handpieces include a tissue cutter, a scaler, a low-speed drill or a high speed drill. The "operative end" of the handpiece is that end which is away from the end which is held and which is used by the dentist to perform the desired operation, e.g. cutting, scaling or drilling. A drill handpiece includes a drill head at the operative end thereof and means within the drillhead for receiving, securely holding and rotating a drill or burr inserted therein. Generally the drill receiving means will be a collet and shaft assembly mounted for low- or high-speed rotation as is known in this field. Means are also provided to rotate the drill receiving means, such as a turbine, including means for transmitting power to the drill rotating means and a control means associated with the power-transmitting means so that when the control means is actuated, power is transmitted to the drill rotating means.

An exemplary scaler handpiece includes a scraper at the operative end of the handpiece along with means to vibrate the scraper at an appropriate rate. Such a scaler is more fully disclosed in U.S. Pat. No. 3,811,190 to Sertich.

The dental handpiece, whether scaler, cutter or drill, also has associated therewith a light source for illuminating the region adjacent the operative end of the dental handpiece.

The control apparatus of the invention comprises (a) means which actuates the light source when power is transmitted to said actuating means;

(b) means for transmitting a signal from the power transmitting means to said actuating means;

(c) delay shutoff means associated with said actuating means to maintain the light source on for a predetermined period of time after termination of transmission of power to the dental handpiece and to cause the light source to be extinguished.

The control apparatus of this invention can be integrated into a dental delivery system or can be an "add on" unit for use in conjunction with an existing dental delivery system. The control unit may be employed in both fluid-driven dental handpiece units as well as electrically-driven units, preferably the former. Thus, the "signal" which is transmitted to the actuating means of (b), above, may be electrical or fluid, e.g. pneumatic. Further, the actuating means of (a), above, is shown in the Figures as a switch, that is, a device which completes or breaks the path of a current to the light source.

In the following description of the drawings, the dental handpiece is depicted as a drill handpiece. It is to be understood, however, that any appropriate powered dental handpiece discussed hereinbefore can be used, with appropriate modifications as would be apparent in view of this disclosure.

FIG. 1 schematically sets forth a specific embodiment of the apparatus of this invention which is a fluid-driven unit, specifically air-driven (pneumatic). As is apparent, other suitable fluids such as nitrogen could also be employed. Dental delivery system 1 has associated therewith a source 2 for supplying pressurized air at about 100 pounds per square inch (psi) pressure. Source 2 can be any means known in the art for this purpose, such as a suitable air pump or compressor. These are commonly used in the dental profession and are well known per se. Such compressors are generally part of the equipment available in a dental or medical building. Thus in a pneumatic system, air provides the power or motive force for the handpiece. The power transmitting means are air lines 4, 4a and 4b which transmit air to handpieces 6, 6a and 6b, respectively. The pressure is adjusted to the desired level by pressure regulator 3, a device readily available from companies such as Watts Regulator Co., 10 Embankment St. Lawrence, Mass. 01841; Humphrey Inc., 9212 Balboa Avenue, San Diego, Calif. 92123; or Clippard Instrument Laboratory, Inc., 7382 Colerain Road, Cincinnati, Ohio 45239.

Air line 4 may pass directly to the handpiece or, as shown in FIG. 1, may first pass through a manifold 5 where a selection can be made between the plurality of handpieces, at least one handpiece 6 being associated with a light source, shown here as a remote light 10, and a fiber-optic transmitting means 8. The other handpieces 6a or 6b are shown as having no light or fiber-optic transmitting means associated therewith. If handpiece 6a or 6b is chosen, the air passes through lines 4a or 4b, respectively. In the apparatus shown in FIG. 1, the manifold 5 may be designed so that the dentist manually selects via a switch (not shown) the handpiece to which air will flow, or the air can automatically flow to the handpiece selected after it is lifted from a hanger (not shown), as generally shown by Austin U.S. Pat. No. 28,649 or Morgan U.S. Pat. No. 3,918,161.

All handpieces have a pneumatically driven turbine within drillhead or housing 9, 9a or 9b to operate the respective drills 7, 7a or 7b and are of a design well known in the art. See for example U.S. Pat. Nos. 3,074,167; 3,120,706, 3,499,223; 3,893,242; 3,946,490; 3,947,966; etc.

Also associated with the power transmitting means 4 for handpiece 6 is a control means such as foot control (not shown) which, when actuated, allows power to be transmitted to the appropriate drill. See U.S. Pat. No. 3,596,102.

To activate the system represented in FIG. 1, when the control means (not shown) is actuated, valve means 26 opens to allow air to flow through lines 4, 4a or 4b and manifold 5 to handpieces 6, 6a or 6b, respectively. Valve means 26 is located between pressure regulator 3 and handpiece 6 and preferably is between manifold 5 and regulator 3 as shown in FIG. 1. Although the valve may be opened or closed by actuating a foot or finger switch, which may be located on the handpiece in the latter case, the valve is preferably incorporated into a pedal operated by the dentist with his foot so that the valve opens when the dentist steps on the foot pedal.

Also associated with the dental handpiece unit in the embodiment of FIG. 1 is a light source consisting of (i) fiber optic means 8, which may be for example a plastic light pipe, a fiber bundle or the like, positioned to transmit light to the region to be drilled and (ii) a light-producing means such as light 10, positioned adjacent the remote end of fiber optic means 8, along with means to energize the light-producing means, such as a source of power 12 for the light 10 and means, e.g. electrical line 11, to transmit power to the light. Light 10 of appropriate small dimension can be integral with handpiece 6 (see, e.g. Hutchinson U.S. Pat. No. 3,634,938) or can be spaced from the handpiece as shown in FIG. 1 (see, e.g. U.S. Pat. No. 3,638,013 to Keller). In the latter case, the light is generally relatively large and will require a cooling fan 13 as shown in FIG. 1. In addition, it is generally advantageous to include rheostat 14 in electrical line 11 to control the intensity of light 10. A suitable fiber optic unit for incorporation with this invention is Model No. UL 30G made by Vicon Inc., Pelham Manor, N.Y. Alternatively, a light of appropriately small dimension may be integral with the handpiece and located at the operative end thereof. In this case, no fiber optic means is needed. See, for example, U.S. Pat. No. 2,038,911 to Stutz et al; French Pat. No. 1,123,034 to Pestel; and German Pat. No. 853,494.

Turning now to the control apparatus of this invention, pneumtically actuated switch 16 associated with electrical line 11 controls actuation of the light-producing means by controlling the flow of electricity to light 10 from power source 12. When switch 16 is closed, power flows from source 12 to actuate cooling fan 13 and lamp 10 which then illuminates one end of fiber optic means 8 thus causing light to be transmitted to the region near drill 7 of handpiece 6 to illuminate the desired area. When switch 16 is open, lamp 10 is off and no light is transmitted along fiber optic means 8.

Air transmittal line 20 transmits a signal, in this case air, from line 4 to switch 16. Air transmittal line 20 joins with line 4 at junction 21 prior to entering handpiece 6 but after exiting from manifold 5 in a simple "T" or "Y" connection as is well known in the art. Alternatively, air transmittal line 20 can be connected directly to the manifold itself. Line 20 may be of any material generally used such as metal or plastic, preferably polyurethane.

Switch 16 closes when air passes through air line 4 and air transmittal line 20 to the right-hand side of pneumatic switch 16.

Delay means 15 is associated with switch 16 to hold the switch closed for a predetermined period of time, and thus maintain light 10 on for that period of time, after the transmission of pressure, in this case air, to the handpiece 6 has ceased. In FIG. 1, one-way valve 22 allows air to be transmitted first to air storage unit 24 and then to pneumatically actuated switch 16, but does not allow air to flow in the opposite direction. The air pressure causes switch 16 to close and activate light 10. Since an excess amount of air is stored in storage unit 24, once the passage of air through valve 22 is terminated, switch 16 will remain closed and the light 10 will remain on for a predetermined period of time depending on the capacity of storage unit 24 and the rate of release through bleeder orifice 25. The stored air will escape to the atmosphere through bleeder orifice 25 thus eventually relieving the pressure on pneumatic switch 16 and allowing it to open whereupon lamp 10 will be extinguished. In this manner, the storage unit, one-way valve and bleeder orifice act as a delay means for maintaining the light source in an energized condition after the transmission of air to handpiece 6 has been stopped.

If desired, a suitable resistor can connect points 17a and 17b to keep a maintenance voltage across the light when switch 16 opens. This expedient decreases the "thermal shock" to the light source and extends the life of the light. However, even with the presence of the resistor, light 10 will be essentially "extinguished" when switch 16 is opened.

A particularly suitable pneumatic delay means and switch are shown in FIG. 3, wherein like numerals as used in FIG. 1 refer to like elements. In FIG. 3 the air storage unit 24, bleeder orifice 25, one way valve 22, and pressure switch 16 are all housed in a single cylindrical unit 19. The air enters through air transmission line 20, inlet 23 and one-way valve 22, which is inside air storage unit 24 instead of outside as in FIG. 1. In FIG. 3 the one-way valve is a "duckbill" valve commonly used in the art. When sufficient air enters the storage unit 24, it causes membrane 18 to deflect which causes contact closure at 17 to allow current to flow through line 11 to energize light 10. Once the air flow is terminated, the "duckbill" valve 22 prevents air in storage unit 24 from escaping through inlet 23 so air escapes through bleeder valve 25 until the pressure on membrane 18 is low enough, i.e. about atmospheric, to break contact at switch 16 and thus stop current flow through line 11. The length of the delay is easily modified by inserting a bleeder orifice having a different orifice size as desired. Generally a time of about 10-15 seconds is considered satisfactory.

In operation with the control apparatus of FIG. 1, the dentist selects which handpiece he desires to use, e.g. handpiece 6, picks it up from its hanger, and presses the foot pedal, not shown, to open valve 26 and allow air to flow through line 4 to handpiece 6 and pneumatic switch 16, to turn on lamp 10, and actuate drill 7. The dentist proceeds with his work, occasionally stopping the drill to view the drilled region with the light transmitted by fiber-optic means 8 from light 10 which stays energized for a predetermined period of time due to air stored in storage unit 24 even though control valve 26 is closed and drill is not operating. When the dentist is finished, he removes his foot from the foot pedal thus stopping air flow to handpiece 6 and switch 16. If desired, he can, once again, examine the drilled area while the light 10 remains on for the predetermined period of time. Light 10 is automatically shut off after a predetermined and controlled amount of air bleeds from storage unit 24. The system may be designed to incorporate an override means (not shown) which, when actuated, allows orifice 25 to open and immediately release sufficient air from storage unit 24, thereby causing switch 16 to open and shut off light 10 essentially simultaneously with the stoppage of drive air flow to the handpiece being used by the dentist. Such override means can, for example, be incorporated into the handpiece cradle in which case the light will be extinguished (if not already extinguished) when the handpiece is replaced on the cradle. Alternatively, the handpiece handle can contain a limit switch which will open the circuit to the lamp.

Turning now to FIG. 2, a schematic diagram of another embodiment of this invention is shown, wherein like numerals as used in FIG. 1 refer to like elements. Again, the unit is pneumatically driven by air supplied from source 2 through pressure regulator 3, line 4, and valve 26 to manifold 5 which has an internal logic system which directs the drive air to the proper handpiece after the dentist has removed handpiece 6 from its associated hanger. As before, one handpiece is associated with fiber-optic means 8 which transmits light from light 10, energized by electricity from source 12. In this embodiment, air line 20 joins transmittal line 4 at juncture 21a before reaching manifold 5 and communicates with pneumatically actuated switch 16 which is closed by the superatmospheric air pressure when valve 26 is opened. Arming switch 32 is in the open condition when handpiece 6 is in hanger 30. Delay means 34 is connected to switch 16 as shown.

In the embodiment shown in FIG. 2, delay means 34 is an electrically actuated delay, preferably of a solid state design. Particularly useful in this regard is a totally solid state timer from SSAC, Inc., P.O. Box 395, Liverpool, N.Y. referred to as the VERSA-TIMER. This delay means may be of fixed time delay mode or may have an external adjustment, e.g. a variable resistor, to modify the predetermined time period chosen as the delay time. In FIG. 2 the delay is shown as a fixed time delay mode.

In operation, when handpiece 6 rests in hanger 30 and valve 26 is closed, the pressure to handpiece 6 and pneumatic switch 16 is atmospheric and thus the fiber-optic illuminating light 10 will be off. Once handpiece 6 is removed from its hanger, spring 29 pulls arm 30a upward to cause switch 32 to contact points 33 and thus arm timer 34. Since valve 26 remains closed, however, no air flows to switch 16 and it remains open and light 10 remains off. To turn light 10 on, the dentist actuates foot control means (not shown) to open valve 26 and allow air to flow to pneumatic switch 16 which closes thereby causing light 10 through circuit 34 to go on.

Thus, if the dentist lifts handpiece 6, but does not actuate foot control switch to open valve 26, the light will not come on. Only after valve 26 is opened and the handpiece is lifted will the light come on. This allows the dentist to pick up the handpiece without risk of "dazzle" should he wish to visually examine the operative end thereof. On the other hand, if the dentist, once having used the handpiece 6, releases the foot control, the pressure collapses, and switch 16 opens, but the delay circuit holds the light on and the dentist can examine the region being drilled using the light on the handpiece 6. The light can be turned off by returning the handpiece to its hanger whereby switch 32 opens to override the delay means 34 and extinguish light 10.

If desired, hanger switch 32 and line 31 associated with hanger 30 can be eliminated, in which case, once the dentist releases the foot control, the pressure collapses but delay circuit 34 holds the lamp on for a predetermined period of time even if the handpiece is returned to hanger 30. The lamp automatically goes out once the period of time is completed. However, in such an arrangement, line 20 would have to connect to air line 4 between manifold 5 and handpiece 6, as discussed hereinbefore regarding FIG. 1, to prevent the light from coming on when handpiece 6a or 6b was lifted from its respective hanger.

It will be apparent that while switch 16 operates in the apparatus set forth in FIGS. 1 and 2 to actuate light 10, the mode of operation to maintain the light on differs in each case. In FIG. 1, light 10 stays on only as long as switch 16 is closed, but when switch 16 opens, light 10 is extinguished. In FIG. 2, on the other hand, light 10 remains on even if switch 16 opens, because the delay means associated with switch 16 maintains the light 10 on for the desired time.

In the embodiments of the apparatus of this invention set forth in FIGS. 1 and 2, valve 26 is actuated by a control means, preferably a foot pedal, which the dentist operates as desired to allow air to flow to handpiece 6 and operate drill 7. The foot pedal may be electrical, pneumatic or mechanical. If electrical, valve 26 is a solenoid valve and depressing the foot pedal causes current to flow to the solenoid and open valve 26. If, on the other hand, the foot pedal is pneumatic, valve 26 is a pneumatic valve and depressing the pedal causes air to flow to pneumatic valve 26 and open it. Alternatively, valve 26 may be mechanical and integral with the foot pedal so that when the foot pedal is depressed valve 26 opens and air flows through line 4 to handpiece 6.

FIG. 4 sets forth a dental delivery system having electrically driven handpieces and an electronic delay 134. Normal customer electrical power is supplied to transformer 103, which reduces the voltage to a safe level and isolates the remainder of the circuit. Handpieces 106, 106a, 106b are driven by electric motors 201, 201a, 201b respectively. Switching manifold 105 is similar in logic performance to pneumatic manifold 5 and allows the dentist to select which handpiece he desires to use by closing appropriate switch 111, 111a or 111b.

In operation, the dentist selects which handpiece he will use and lifts, e.g., handpiece 106 from its hanger, not shown. Switch 111 is closed either manually or automatically to ready the line 104 to receive current. When the dentist wishes to start drilling he closes switch 126, preferably by pressing a foot pedal (not shown) and electricity then flows to electric motor 201 in handpiece 106 to actuate drill 107 in housing 109. At the same time electricity is transmitted to electrical relay switch 116 via line 120 which closes to complete the circuit which actuates light 110. Light is transmitted along fiber-optic means 108 to the operative end of handpiece 106 to illuminate the region being drilled. In addition handpiece 106 can be associated with an arming switch such as shown in FIG. 2 and discussed hereinbefore.

Turning now to FIG. 5, one can see a detailed schematic circuit diagram of a representative electric delay means 234 of solid state design having a fixed time mode suitable for use in the apparatus of this invention. Such a delay means is readily employed, in the apparatus shown in FIGS. 2, 4 and 8 and may be readily modified as desired by one skilled in this art.

In operation, electricity is supplied by transformer 212 to a reed switch 204 which is enclosed in coils 205. When the current flowing through coils 205 is sufficiently large, switch 204 will close completing the circuit between points 206 and 208 thus allowing current to flow through line 217 to energize light 218. As long as voltage across coil 205 remains above a predetermined level, enough current flows to keep switch 204 closed and the light remains on. When the voltage across coil 205 drops below a predetermined level, current flow decreases, switch 204 opens and light 218 is extinguished.

Transformer 212 supplies power not only to energize the light 218 but also to operate the delay circuit for delay means 234. In operation, current is constantly supplied from transformer 212 to a full wave bridge rectifier 236 in the delay circuit to convert the AC output of the transformer to DC current and operate the delay circuit. When the voltage coming from operational amplifier 222 at point 220 is sufficiently large, for example, 3.3 volts direct current, switch 204 will close and light 218 will be on, but when the voltage at point 220 drops below a certain set value, for example, 0.3 volts direct current, switch 204 will open thus extinguishing light 218. Thus, it is seen that operational amplifier 222 (for example, Item No. LM 358 from Texas Inst. Dallas, Tx.) operates in essentially two states to provide the necessary voltage to operate switch 204. When the voltage at point 224 is greater than at point 226, the output of the amplifier, that is the voltage at point 220 is approximately 0.3 volts direct current. At this point the switch 204 will be open. When the voltage at 224 is less than the voltage at 226 the output of amplifier 222 is then about 3.3 volts DC, which is sufficient to close the switch 204 and allow light 218 to go on. Note that rectifier 236 is needed if the input current to transformer 212 is Ac current. If, on the other hand, direct current is available, transformer 212 and rectifier 236 are not needed.

When pressure switch 216 (corresponding to switch 16 in FIGS. 2, 4 or 8) is closed, that is the dentist has pressed the foot pedal to allow air pressure to flow to pressure switch 216 and close the switch, the voltage at 226 will become the same as the voltage at 228 or approximately 6 volts direct current. Since at that point the voltage at 224 will be less than the voltage at 226, the voltage at 220 will become 3.3 volts DC, thus providing sufficient current through coil 205 to close Reed switch 204 and energize light 218. When switch 216 opens due to a lack of air pressure, the voltage at 226 will not drop to 0 immediately because of a charge stored in capacitor 230. The voltage at 226 will slowly decrease through resistor-capacitor-ground combination 230, 232, 233. When the voltage at 226 finally becomes less than the voltage at 224, the output of amplifier 222 will be 0.3 volts DC, thus allowing switch 204 to swing open and extinguish light 218. The time required for the voltage at 226 to decrease to below the voltage at 224 after switch 216 opens determines the time delay period of the circuit. Preferably this time is about 10-15 seconds. A filter capacitor 237 is employed to smooth out ripple output of the bridge rectifier and a diode 238 is used to prevent current from feeding back into the operational amplifier 222. Resistors 240, 242 and ground 244 are chosen to give a voltage of 0.3 volts at point 224.

The line 215 extending from contact 214 provides access to set up a series of delay means modules each of which can be used with an individual handpiece and light source for illuminating the region adjacent the operative end of the handpiece.

As an alternative to locating the light 10 spaced from handpiece 6 as shown in FIGS. 1, 2 and 4, the light may be located in the handpiece as shown in schematic FIG. 6 or 8 (e.g. in a handpiece module which readily fits into the handpiece), or in the handpiece adjacent the operative end when fiber optics are not utilized as shown in FIG. 9.

When the light is mounted in the handpiece, it will be appreciated that the delay means prevents the light from staying on for a long period of time when no air is flowing, thus preventing the handpiece from overheating due to heat generated by the light source.

In keeping with the invention, it can be seen from FIG. 6 that the apparatus can be designed to be used with a plurality of dental handpieces, each having a light producing means and fiber optic means integral with the handpiece. In FIG. 6 like numerals refer to like elements as found in FIGS. 1 and 2.

In operation, the apparatus set forth schematically in FIG. 6 is similar to that set forth in the previous Figures. Pressurized air from source 2 is reduced by pressure regulator valve 3 and enters line 4 where air flow to handpieces 6, 6a and 6b is regulated by valve 26 which is operated by a suitable means, preferably on a foot pedal, not shown. As the pedal is depressed valve 26 opens and allows air to flow to manifold 5 which is designed to allow the air to flow through lines 4, 4a or 4b when the corresponding handpiece 6, 6a or 6b is picked up. As handpiece 6 is lifted from its hanger, manifold 5 adjusts to allow air to flow to line 4 and handpiece 6. Switch 40 is designed to close when handpiece 6 is picked up, thus allowing current to flow to lamp 10 if switch 16 is closed. As air is flowing through line 4, it also flows through "T" connection 21a and line 20 to pneumatic delay means 15 via one-way valve 22 thereby causing switch 16 to close, thus, allowing current to flow from the power source 12 to energize light 10. The illumination produced by light 10 is transmitted along fiber optic means 8 to the region near drill 7 so that the dentist can see the area which is being drilled.

When valve 26 is closed, the flow of air to delay means 15 and handpiece 6 ceases, but the air contained in storage unit 24 keeps switch 16 closed for a predetermined period of time while the air bleeds through orifice 25. Thus, the dentist can view the area that has just been drilled with the aid of light eminating from fiber optic means 8. When handpiece 6 is replaced on the hanger, switch 40 opens thereby automatically extinguishing light 10 if the predetermined period of time has not yet expired. Rheostat 14 can be used to adjust the intensity of light emitted by lights 10, 10a or 10b.

In the dental handpiece system of FIG. 6, it is possible that lights 10, 10a and 10b could light all at one time if the dentist lifted all three handpieces from their respective hangers and opened valve 26. To avoid such a result, the system can be modified as shown in FIG. 7. In the condition shown all three handpieces have been lifted so that all three single pole, double throw switches 40, 40a, and 40b are closed. However, even if switch 16 is closed, only light 10 would light because there would be no complete circuit for the other handpiece lights. This arrangement is particularly valuable if the power from source 12 is sufficient for only one light.

In further keeping with the invention, a particularly preferred arrangement for a plurality of handpieces, each having its own light producing means is shown schematically in FIG. 8, where like numerals refer to like elements as in FIG. 6 and like elements concerning the electric delay means of FIG. 5. In FIG. 8 individual delay means 34, 34a are associated with each individual handpiece 6, 6a, respectively. In FIG. 8 only two handpieces are shown as being associated with manifold 5; however, it is to be understood that any number of handpieces can be associated with manifold 5 as required by the individual dentist. In operation the apparatus set forth schematically in FIG. 8 is similar to the apparatus set forth previously in FIG. 6. Valve 26 is opened by pressing foot pedal, not shown, to allow air to flow to the manifold. By lifting the handpiece 6 off its hanger, not shown, the logic system of manifold 5 directs the air from the manifold to the lifted handpiece. As the air flows through line 4, it also flows through line 20 to pressure switch 16, which closes, to energize light 10 through delay means circuit 34 as described in the discussion of FIG. 5. Light produced is transmitted via light transmitting means 8 to the region of drill 7 so that the dentist can see the area which is being drilled in the patient's mouth. Once the foot pedal is released, valve 26 closes and the air flow stops and switch 16 opens, but light 10 remains on for the predetermined period of time due to the action of delay means 34 in keeping current flowing to light 10. Instead of using handpiece 6 the dentist can also use handpiece 6a which operates similarly.

In addition to the individual delay means associated with each handpiece, the apparatus can optionally include a separate circuit for a remote lighting means such as exploratory probe 78 which is operated independently of handpieces 6 and 6a. In operation, closing switch 70 allows current to flow from power source 12 to energize light 74. In this embodiment, the illumination from light 74 is transmitted along fiber optic means 76 to probe end 79 which the dentist employs, independently of the use of the handpieces, to examine a patient's mouth. Another embodiment would illuminate via light 74 positioned at the end of probe 78 and would not require a fiber optic means. Rheostat 80 is used to adjust the intensity of light 74.

Still another embodiment of the apparatus of this invention is schematically shown in FIG. 9. In this embodiment, once handpiece 6a is picked up, valve 26 is opened to allow air flow through manifold 5, lines 4a, 46, 48, through one-way valves 47 and 22 to air storage means 24 to cause diaphragm 18 to expand and close switch 16. As air passes through line 48, which is in fluid communication with line 4a, accordian element 49 expands until it forces toggle switch 50 to contact point 51a, thus completing the circuit and allowing lamp 10a to light. Switch 50 and contacts 51a, 51b comprise a bistable single pole, double throw switch with no center off position. Bellows 49 only pushes switch 50 to contact 51a while bellows 43 only pushes switch 50 to contact 51b and the only time switch 50 moves from one position to another is when the dentist changes handpieces. Once the flow of air to handpiece 6a is stopped by causing valve 26 to close, accordian element 49 contracts, leaving the switch 50 contacting point 51b. Air storage unit 24 retains switch 16 in a closed position and allows the light 10 to remain on for a predetermined period of time until the air in the storage unit bleeds out through orifice 25.

If the dentist wishes to use handpiece 6 after he replaces handpiece 6a, he picks up handpiece 6 and opens valve 26 to allow air to flow through manifold 5, lines 4, 40, 42 through one-way valves 41, 22 to air storage 24 and diaphragm 18 thus closing switch 16. Air expands accordian element 43 to push switch 50 into contact 51b thus completing the circuit and causing light 10 to light. When the dentist closes valve 26, air flow ceases but switch 50 remains contacting point 51b and light 10 remains on for a predetermined period of time as discussed before.

FIG. 10 sets forth an alternative delay means which can be used in the apparatus of this invention, especially if the light is within the handpiece. In operation, when the handpiece is picked up and valve 26 opened, air flows to lines 4 and 4d to cause diaphragm 62b to expand and reset thermal switch 62. Current from source 12 flows to light 10, simulator resistor 60, and resettable thermal switch 62. Light 10 will remain on as long as switch 62 is closed to complete the circuit. When air flows through air line 4, the air passing simulator resistor 60 draws heat away from the resistor thus keeping the temperature down, maintaining the thermal switch 62 closed to maintain the light on. When the air is shut off, the pressure on diaphragm 62b drops and the heat from the resistor 60 rises until it is sufficient to cause thermal switch 62 to open and thus turn light 10 off. In this manner the light will be kept on for a predetermined period of time which is determined by the physical characteristics of thermal switch 62, the heat generated by current flowing through resistor 60, and the proximity of one to the other. When thermal switch 62 opens, plunger 62a will extend upwardly because there is no air pressure on diaphragm 62b to prevent its upward thrust. When air is resupplied to line 4, it also is supplied to line 4d and diaphragm 62b to force plunger 62a downwardly and reset thermal switch 62.

An analogous system may be employed where light 10 is again located in a handpiece. In this case a thermocouple can be employed in place of the thermal switch. Heat from light 10 causes the thermocouple to open at its predetermined or built-in limit, and thus stop current flow. The air flow pattern can be designed to cool the handpiece enclosure and thermocouple so that, as long as air flows, the temperature of the thermocouple remains sufficiently low and the light remains on. However, when air flow stops, the temperature rises to a point where the thermocouple opens, thus stopping current flow and turning off the light.

Turning now to FIG. 11, we see a perspective view of the apparatus of this invention which corresponds to the schematic diagram set forth in FIG. 8. Box 140 contains a transformer and protection circuits for the apparatus of the invention. Electrical line 142 leads from box 140 to box 144 which contains the switch for the light-producing means and the delay means associated with that switch. Also associated with the switch and delay means is air transmittal line 146 connected to means 148 for transmitting a signal from air line 150 to the pneumatic switch and delay means in box 144. In this case means 148 further includes a conduit for directing air from air line 150 to the pneumatic delay means contained in box 144. Electrical line 152 carries the current to handpiece 154 (which corresponds to handpiece 6 in FIG. 8) to energize the light, not shown, contained in the handpiece. When the switch (corresponding to 16 in FIG. 8) not shown, is closed, current flows through line 152 to energize light in the handpiece where the light is transmitted by fiber optic means to the operative end of the handpiece. Additional control unit 158 for another handpiece can be added onto box 144 by plugging jacks 160 into receptacles 161 to thereby tie into the electrical circuitry. Units 158 and 144 can be detachably mounted if desired. Transmittal line 163 is readily connected to air line 162 by T connection 164. The delay means and switch for handpiece 166 are contained in box 158. Current to energize light (not shown) in handpiece 166 runs through line 168.

Box 144 contains an electrical connection to which electrical cable 170 connects to supply power to probe 172 having light-emitting surface 174 and internal light (not shown). The probe can employ fiber optic means or may use a sufficiently small bulb to obviate the need for fiber optic means. The electrical current can be controlled either by a hanger switch or by a switch on the probe handle (neither shown).

Thus it is apparent that there has been provided, in accordance with the invention, a control apparatus for use with a dental handpiece and associated equipment that satisfies the advantages set forth above. While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and scope of the appended claims.

The subject matter claimed is:

1. An apparatus for controlling the actuation of a light source for illuminating the work zone adjacent the operative end of a dental handpiece, the dental handpiece having associated therewith means for transmitting power to the operative end of the handpiece, control means associated with the power-transmitting means so that when the control means is actuated, power is transmitted to the operative end of the handpiece, and a light source for illuminating the work zone adjacent the operative end of the dental handpiece;

said control apparatus comprising:
(a) means for actuating the light source when a signal is transmitted to said actuating means from the power transmitting means;
(b) means for transmitting the signal from the power transmitting means to said actuating means and
(c) delay shutoff means associated with said actuating means for maintaining the light source on for a predetermined period of time after transmission of power to the operative end of the handpiece is terminated and then causing the light source to be extinguished at the end of said predetermined period of time.

2. The control apparatus of claim 1 wherein the operative end of the handpiece is electrically driven, said actuating means is electrically actuated and said delay means is electrically operated.

3. The control apparatus of claim 1 wherein the operative end of handpiece is pneumatically driven and said actuating means is pneumatically actuated.

4. The control apparatus of claim 1 wherein said delay means is electrically operated.

5. The control apparatus of claim 4 wherein said delay means is of solid state design.

6. The apparatus of claim 4 wherein said electrically operated delay means comprises
a first electrical line for conducting a source of direct current to said actuating means;
an amplifier;
a second electrical line from said actuating means to said amplifier;
a capacitor conductively connected to said second line for storing a predetermined amount of electric energy, along with a first resistor and a ground for discharging the energy stored in said capacitor at a predetermined rate;
said amplifier conductively connected to said second line after said capacitor/first resistor/ground combination;
a third electrical line leading from the output of said amplifier;
a reed switch;
coils surrounding said reed switch, said coils conductively connected to said third line; and
a fourth electrical line conductively connecting said first electrical line to said amplifier through at least one second resistor whereby when said actuating means allows current to flow from said first electrical line through said actuating means to said second line, said capacitor and said amplifier so that electrical energy is stored in said capacitor, and the voltage at said second electrical line at the input to said amplifier is sufficiently greater than the voltage at the input to said amplifier at said fourth electrical line to cause the output voltage from said amplifier to be sufficient to cause current to flow through said coils to actuate said reed switch and complete a circuit to energize the light source, and when said actuating means stops current flow to said second line, the electrical energy stored in said capacitor discharges at a predetermined rate until the voltage at said second line leading to said amplifier becomes less than the voltage at said fourth line leading to said amplifier and the voltage from said amplifier drops below a predetermined value so that the current flowing through said coils is insufficient to maintain said reed switch closed and said reed switch opens whereupon the light is extinguished.

7. The apparatus of claim 6 wherein a rectifier to transform alternating current into direct current is connected to said first line.

8. The apparatus of claim 6 wherein said actuating means is a pneumatically actuated switch.

9. The control apparatus of claim 1 wherein said delay means is pneumatically operated.

10. The control apparatus of claim 1 wherein said delay means is fluid operated and comprises a fluid storage unit, means to transmit fluid to said fluid storage unit, a one-way valve associated with said fluid storage unit so that fluid is allowed to enter said fluid storage unit through said one-way valve from said fluid transmitting means, a bleeder orifice associated with said fluid storage unit to allow fluid to escape from said fluid storage unit at a predetermined rate, said fluid storage unit being associated with said actuating means so that fluid stored within said fluid storage unit maintains the light source on for a predetermined period of time until sufficient fluid escapes therefrom through said fluid bleeder orifice to permit said actuating means to stop current flow to said light source and thereby extinguish it.

11. The apparatus of claim 10 wherein said actuating means is a pneumatically actuated switch.

12. The apparatus of claim 1 wherein said actuating means is a pneumatically actuated switch.

13. A light-producing and controlling apparatus for use with a dental handpiece having associated therewith means for transmitting power to the operative end of the handpiece and a control means associated with the power transmitting means so that when the control means is actuated, power is transmitted to the operative end of the handpiece, said light-producing and controlling apparatus comprising:
(a) a light source for illuminating the region adjacent the operative end of the handpiece;
(b) a means for actuating the light source when a signal is transmitted to said actuating means from the power transmitting means;
(c) means for transmitting said signal from the power transmitting means to said actuating means; and
(d) delay shutoff means associated with said actuating means for maintaining said light source on for a predetermined period of time after transmission of power to the operative end of the dental handpiece is terminated and then causing said light source to be extinguished at the end of said predetermined period of time.

14. The apparatus of claim 13 wherein the operative end of the dental handpiece is electrically driven, said actuating means is electrically actuated and said delay means is electrically operated.

15. The apparatus of claim 13 wherein the operative end of the handpiece is pneumatically driven and said actuating means is pneumatically actuated.

16. The apparatus of claim 13 wherein said delay means is electrically operated.

17. The apparatus of claim 16 wherein said delay means is of solid state design.

18. The apparatus of claim 16 wherein said electrically operated delay means comprises
a first electrical line for conducting a source of direct current to said actuating means;
an amplifier;
a second electrical line from said actuating means to said amplifier;
a capacitor conductively connected to said second line for storing a predetermined amount of electric energy, along with a first resistor and a ground for discharging the energy stored in said capacitor at a predetermined rate;
said amplifier conductively connected to said second line after said capacitor/first resistor/ground combination;
a third electrical line leading from the output of said amplifier;
a reed switch;
coils surrounding said reed switch, said coils conductively connected to said third line; and
a fourth electrical line conductively connecting said first electrical line to said amplifier through at least one second resistor, whereby when said actuating means allows current to flow from said first line through said actuating means to said second line, said capacitor and said amplifier so that electrical energy is stored in said capacitor, and the voltage at said second electrical line at the input to said amplifier is sufficiently greater than the voltage at the input to said amplifier at said fourth electrical line to cause the output voltage from said amplifier to be sufficient to cause current to flow through said coils to actuate said reed switch and complete a circuit to energize said light source, and when said actuating means stops current flow to said second line, the electrical energy stored in said capacitor discharges at a predetermined rate until the voltage at said second line leading to said amplifier becomes less than the voltage at said fourth line leading to said amplifier and the voltage from said amplifier drops below a predetermined value so that the current flowing through said coils is insufficient to to maintain said reed switch closed and said reed switch opens whereupon said light source is extinguished.

19. The apparatus of claim 18 wherein a rectifier to transform alternating current into direct current is connected to said first line.

20. The apparatus of claim 18 wherein said actuating means is a pneumatically actuated switch.

21. The apparatus of claim 13 wherein said delay means is pneumatically operated.

22. The apparatus of claim 13 wherein said delay means is fluid operated and comprises a fluid storage unit, means to transmit fluid to said fluid storage unit, a one-way valve associated with said fluid storage unit so that fluid is allowed to enter said fluid storage unit through said one-way valve from said fluid transmitting means, a bleeder orifice associated with said fluid storage unit to allow fluid escape from said fluid storage unit at a predetermined rate, said fluid storage unit being associated with said actuating means so that fluid stored within said fluid storge unit maintains said light source on for a predetermined period of time until sufficient fluid escapes therefrom through said bleeder orifice to permit said actuating means to stop current flow to said light source and thereby extinguish it.

23. The apparatus of claim 22 wherein said actuating means is a pneumatically actuated switch.

24. The apparatus of claim 13 wherein said actuating means is a pneumatically actuated switch.

25. The apparatus of claim 13 wherein said light source is remote from the handpiece and fiber optic means transmits light from said light source to the region adjacent the operative end of the handpiece.

26. The apparatus of claim 13 wherein said light source is integral with the handpiece.

27. The apparatus of claim 22 wherein said light source is remote from the operative end of the dental handpiece and fiber optic means transmits light from said light source to the region adjacent the operative end of the dental handpiece.

28. A dental handpiece apparatus which comprises
(a) a dental handpiece having an operative end and means for transmitting power to said handpiece and its operative end;
(b) light source for illuminating the region adjacent the operative end of said handpiece;
(c) means for actuating said light source when a signal is transmitted to said actuating means from said power transmitting means;
(d) means to transmit a signal from said power transmitting means for said handpiece to said actuating means; and
(e) delay shutoff means associated with said actuating means for maintaining said light source on for a predetermined period of time after transmission of power to the operative end of said handpiece is terminated and then causing said light source to be extinguished at the end of said predetermined period of time.

29. The apparatus of claim 28 wherein the operative end of said handpiece means is electrically driven, said switch is electrically actuated, and said delay means is electrically operated.

30. The apparatus of claim 28 wherein the operative end of said handpiece is pneumatically driven and said actuating means is pneumatically actuated.

31. The appratus of claim 28 wherein said delay means is electrically operated.

32. The apparatus of claim 31 wherein said delay means is of solid state design.

33. The apparatus of claim 31 wherein said electrically operated delay means comprises
a first electrical line for conducting a source of direct current to said actuating means;
an amplifier;
a second electrical line from said actuating means to said amplifier;
a capacitor conductively connected to said second line for storing a predetermined amount of electric energy, along with a first resistor and a ground for discharging the energy stored in said capacitor at a predetermined rate;

said amplifier conductively connected to said second line after said capacitor/first resistor/ground combination;

a third electrical line leading from the output of said amplifier;

a reed switch coils surrounding said reed switch, said coils conductively connected to said third line; and a fourth electrical line conductively connecting said first electrical line to said amplifier through at least one second resistor, whereby when said actuating means allows current to flow from said first line through said actuating means to said second line, said capacitor and said amplifier so that electrical energy is stored in said capacitor, and the voltage at said second electrical line at the input to said amplifier is sufficiently greater than the voltage at the input to said amplifier at said fourth electrical line to cause the output voltage from said amplifier to be sufficient to cause current to flow through said coils to actuate said reed switch and complete a circuit to energize the light source, and when said actuating means stops current flow to said second line, electrical energy stored in said capacitor discharges at a predetermined rate until the voltage at said second line leading to said amplifier becomes less than the voltage at said fourth line leading to said amplifier and the voltage from said amplifier drops below a predetermined value so that current flowing through said coils is insufficient to maintain said reed switch closed and said reed switch opens whereupon the light is extinguished.

34. The apparatus of claim 28 wherein said delay means is pneumatically operated.

35. The apparatus of claim 28 wherein said delay means is fluid operated and comprises a fluid storage unit, means to transmit fluid to said storage unit, a one-way valve associated with said fluid storage unit so that fluid is allowed to enter said fluid storage unit through said one-way valve from said fluid transmitting means, a bleeder orifice associated with said fluid storage unit to allow fluid to escape from said fluid storage unit at a predetermined rate, said fluid storage unit being associated with said actuating means that the fluid stored within said fluid storage unit maintains said light-producing means on for a predetermined time until sufficient fluid escapes therefrom through said bleeder orifice to permit said actuating means to stop current flow to said light source and thereby extinguish it.

36. The apparatus of claim 28 wherein said light source is remote from the handpiece and fiber optic means transmits light from said light source to the region adjacent the operative end of said handpiece.

37. The apparatus of claim 28 wherein said light source is integral with said dental handpiece.

38. The apparatus of claim 37 wherein said light source is remote from the operative end of said handpiece and fiber optic means transmits light from said light source to the region adjacent the operative end of said dental handpiece.

39. A control apparatus for controlling the actuation of a light source for illuminating the region adjacent the operative end of a dental handpiece having associated therewith a fluid-driven turbine, means associated with the turbine to securely receive and to rotate a drill when the turbine is driven by the fluid, means for transmitting drive fluid to the turbine, a control means associated with the fluid-transmitting means so that when the control means is actuated the turbine is driven by the fluid, light-producing means, and fiber optic means to transmit light from the light-producing means to the region adjacent the operative end of the handpiece for illuminating the area to be drilled;

said control apparatus comprising:

(a) a fluid-actuated switch for actuating the light-producing means when fluid is transmitted to said fluid-actuated switch from the drive fluid transmitting means;

(b) means for transmitting fluid from the drive fluid transmitting means to said fluid-actuated switch; and (c) delay shutoff means associated with said fluid-actuated switch for maintaining the light-producing means on for a predetermined period of time after transmission of fluid to the turbine is terminated and then causing the light source to be extinguished at the end of said predetermined period of time.

40. The apparatus of claim 39 wherein the fluid is air.

41. The apparatus of claim 39 wherein said delay means is electrically operated.

42. The apparatus of claim 41 wherein said electrically operated delay means comprises a rectifier to transform alternating current into direct current;

a first electrical line from said rectifier to said fluid-actuated switch;

an amplifier;

a second electrical line from said fluid-actuated switch to said amplifier;

a capacitor conductively connected to said second line for storing a predetermined amount of electric energy, along with a first resistor and a ground for discharging the energy stored in said capacitor at a predetermined rate;

said amplifier conductively connected to said second line after said capacitor/first resistor/ground combination;

a third electrical line leading from the output of said amplifier;

a reed switch;

coils surrounding a reed switch, said coils conductively connected to said third line; and a fourth electrical line conductively connecting said first electrical line to said amplifier through at least one second resistor so that when said fluid-actuated switch closes current flows from said rectifier through said fluid-actuated switch to said capacitor and said amplifier so that electrical energy is stored in said capacitor and the voltage at said second electrical line at the input to said amplifier is sufficiently greater than the voltage at the input to said amplifier at said fourth electrical line to cause the output voltage from said amplifier to be sufficient to cause current to flow through said coils to actuate said reed switch and complete a circuit to energize the light source, and when said fluid-actuated switch opens the electrical energy stored in said capacitor discharges at a predetermined rate until the voltage at said second line leading to said amplifier becomes less than the voltage at said fourth line leading to said amplifier and the voltage from said amplifier drops below a predetermined value so that the current flowing through said coils is insufficient to maintain said reed closed and said reed switch opens whereupon the light is extinguished.

43. The apparatus of claim 39 wherein said delay means is pneumatically operated.

44. The apparatus of claim 39 wherein said delay means is fluid operated and comprises a fluid storage unit, means to transmit fluid to said fluid storage unit, a one-way valve associated with said fluid storage unit so that fluid is allowed to enter said fluid storage unit through said one-way valve from said fluid transmitting means, a bleeder orifice associated with said fluid storage unit to allow fluid to escape from said fluid storage unit at a predetermined rate, said fluid storage unit being associated with said fluid-actuated switch so that the fluid stored within said storage unit maintains said light-producing means on for a predetermined time until sufficient fluid escapes therefrom through said bleeder orifice to permit said fluid-actuated switch to open.

45. A fiber optic light-producing and controlling apparatus for use with a dental handpiece having associated therewith a fluid-driven turbine, means associated with the turbine to securely receive and to rotate a drill when the turbine is driven by the fluid, means to transmit drive fluid to the turbine, control means associated with the fluid-transmitting means so that when the control means is actuated, fluid is transmitted to the turbine; said fiber optic light-producing and controlling aparatus comprising:
(a) light source;
(b) fiber optic means for transmitting light from said light source to the region adjacent the operative end of the handpiece for illuminating the area to be drilled;
(c) a fluid-actuated switch for actuating the light-producing means when fluid is transmitted to said fluid-actuated switch from the fluid transmitting means;
(d) means for transmitting fluid from the means for transmitting fluid to the turbine to said fluid-actuated switch; and
(e) delay shutoff means associated with said fluid-actuated switch for maintaining said light source on for a predetermined period of time after transmission of fluid to the turbine is terminated and then causing the light source to be extinguished at the end of said predetermined period of time.

46. The apparatus of claim 45 wherein the fluid is air.

47. The apparatus of claim 45 wherein said delay means is electrically operated.

48. The apparatus of claim 47 wherein said electrically operated delay means comprises
a rectifier to transform alternating current into direct current;
a first electrical line from said rectifier to said second switch;
an amplifier;
a second electrical line from said fluid-actuated switch to said amplifier;
a capacitor conductively connected to said second line for storing a predetermined amount of electric energy, along with a first resistor and a ground for discharging the energy stored in said capacitor at a predetermined rate;
said amplifier conductively connected to said second line after said capacitor/first resistor/ground combination;
a third electrical line leading from the output of said amplifier;
a reed switch;
coils surrounding said reed switch, said coils conductively connected to said third line; and
a fourth electrical line conductively connecting said first electrical line to said amplifier through at least one second resistor so that when said fluid-actuated switch closes current flows from said rectifier through said fluid-actuated switch to said capacitor and said amplifier so that electrical energy is stored in said capacitor and the voltage at said second electrical line at the input to said amplifier is sufficiently greater than the voltage at the input to said amplifier at said fourth electrical line to cause the output voltage from said amplifier to be sufficient to cause current to flow through said coils to actuate said reed switch and complete a circuit to energize the light source, and when said fluid-actuated switch opens, the electrical energy stored in said capacitor discharges at a predetermined rate until the voltage at said second line leading to said amplifier becomes less than the voltage at said fourth line leading to said amplifier and the voltage from said amplifier drops below a predetermined value so that the current flowing through said coils is insufficient to maintain said reed switch closed and said reed switch opens whereupon the light is extinguished.

49. The apparatus of claim 45 wherein said delay means is pneumatically operated.

50. The apparatus of claim 45 wherein said delay means is fluid operated and comprises a fluid storage unit, means to transmit fluid to said fluid storage unit, a one-way valve associated with said fluid storage unit so that fluid is allowed to enter said fluid storage unit through said one-way valve from said fluid transmitting means, a bleeder orifice associated with said fluid storage unit to allow fluid to escape from said fluid storage unit at a predetermined rate, said fluid storage unit being associated with said fluid-actuated switch so that fluid stored within said fluid storage unit maintains said light-producing means on for a predetermined period of time until sufficient fluid escapes therefrom through said bleeder orifice to permit said fluid-actuated switch to open and extinguish said light.

51. The apparatus of claim 45 wherein said light source and said fiber optic means are integral with the handpiece.

52. A fiber optic equipped dental handpiece apparatus which comprises:
(a) a dental handpiece having a fluid-driven turbine and means associated with said turbine to securely receive and to rotate a drill when said turbine is driven by a fluid;
(b) means for transmitting fluid to said turbine;
(c) a light source integral with said handpiece;
(d) fiber optic means for transmitting light from said light source to the operative end of said handpiece for illuminating the area to be drilled;
(e) a fluid-actuated switch for actuating said light source;
(f) means to transmit fluid from said fluid transmitting means of (b) to said fluid-actuated switch, whereby said fluid-actuated switch closes when fluid is transmitted thereto, thereby actuating said light source; and (g) delay shutoff means associated with said fluid-actuated switch for maintaining said light source on for a predetermined period of time after transmission of fluid to said turbine is terminated and then causing said light source to be extinguished at the end of said predetermined period of time.

53. The apparatus of claim 52 wherein the fluid is air.

54. The apparatus of claim 52 wherein said light source and said fiber optic means are integrated into said dental handpiece.

55. The apparatus of claim 52 wherein said delay means is electrically operated.

56. The apparatus of claim 55 wherein said electrically operated delay means comprises a rectifier to transform alternating current into direct current;

a first electrical line from said rectifier to said fluid-actuated switch;

an amplifier;

a second electrical line from said fluid-actuated switch to said amplifier;

a capacitor conductively connected to said second line for storing a predetermined amount of electric energy, along with a first resistor and a ground for discharging the energy stored in said capacitor at a predetermined rate;

said amplifier conductively connected to said second line after said capacitor/first resistor/ground combination;

a third electrical line leading from the output of said amplifier;

a reed switch;

coils surrounding a reed switch, said coils conductively connected to said third line; and a fourth electrical line conductively connecting said first electrical line to said amplifier through at least one second resistor so that when said fluid-actuated switch closes current flows from said rectifier through said fluid-actuated switch to said capacitor and said amplifier so that electrical energy is stored in said capacitor and the voltage at said second electrical line at the input to said amplifier is sufficiently greater than the voltage at the input to said amplifier at said fourth electrical line to cause the output voltage from said amplifier to be sufficient to cause current to flow through said coils to actuate said reed switch and complete a circuit to energize the light source and when said fluid-actuated switch opens the electrical energy stored in said capacitor discharges at a predetermined rate until the voltage at said second line leading to said amplifier becomes less than the voltage at said fourth line leading to said amplifier and the voltage from said amplifier drops below a predetermined value so that the current flowing through said coils is insufficient to maintain said reed switch closed and said reed switch opens whereupon the light is extinguished.

57. The apparatus of claim 52 wherein said delay means is pneumatically operated.

58. The apparatus of claim 52 wherein said delay means is fluid operated and comprises a fluid storage unit, means to transmit fluid to said fluid storage unit, a one-way valve associated with said fluid storage unit so that fluid is allowed to enter said fluid storage unit through said one-way valve from said fluid transmitting means, a bleeder orifice associated with said fluid storage unit to allow fluid to escape from said fluid storage unit at a predetermined rate, said fluid storage unit being associated with said fluid-actuated switch so that the fluid stored within said fluid storage unit maintains said light-producing means on for a predetermined time until sufficient fluid escapes therefrom through said bleeder orifice to permit said fluid-actuated switch to open.

* * * * *